(12) United States Patent
Whipple

(10) Patent No.: US 9,820,866 B2
(45) Date of Patent: Nov. 21, 2017

(54) EXPANDABLE SPINAL IMPLANT

(71) Applicant: Amendia, Inc., Marietta, GA (US)

(72) Inventor: Dale Whipple, Acworth, GA (US)

(73) Assignee: Amendia, Inc., Marietta, GA (US)

( * ) Notice: Subject to any disclaimer, the term of this patent is extended or adjusted under 35 U.S.C. 154(b) by 94 days.

(21) Appl. No.: 15/150,548

(22) Filed: May 10, 2016

(65) Prior Publication Data
US 2016/0250033 A1 Sep. 1, 2016

Related U.S. Application Data

(62) Division of application No. 14/259,639, filed on Apr. 23, 2014, now Pat. No. 9,364,344.

(51) Int. Cl.
*A61F 2/44* (2006.01)
*A61F 2/46* (2006.01)
*A61F 2/30* (2006.01)

(52) U.S. Cl.
CPC .......... *A61F 2/447* (2013.01); *A61F 2/4455* (2013.01); *A61F 2/4611* (2013.01); *A61F 2002/30522* (2013.01); *A61F 2002/30556* (2013.01); *A61F 2002/30579* (2013.01)

(58) Field of Classification Search
CPC ...... A61F 2/4455; A61F 2/447; A61F 2/4611; A61F 2002/30522
See application file for complete search history.

(56) References Cited

U.S. PATENT DOCUMENTS

| 5,658,335 | A  | 8/1997  | Allen           |
|-----------|----|---------|-----------------|
| 5,723,013 | A  | 3/1998  | Jeanson et al.  |
| 6,176,881 | B1 | 1/2001  | Schaer et al.   |
| 6,176,882 | B1 | 1/2001  | Biedermann et al. |
| 6,733,535 | B2 | 5/2004  | Michelson       |
| 7,094,257 | B2 | 8/2006  | Mujwid et al.   |
| 7,648,529 | B2 | 1/2010  | An et al.       |
| 7,758,644 | B2 | 7/2010  | Trieu           |
| 7,828,849 | B2 | 11/2010 | Lim             |
| 7,850,733 | B2 | 12/2010 | Baynham et al.  |
| 7,879,096 | B2 | 2/2011  | Dickson et al.  |
| 7,909,870 | B2 | 3/2011  | Kraus           |
| 8,062,375 | B2 | 11/2011 | Glerum et al.   |
| 8,105,382 | B2 | 1/2012  | Olmos           |
| 8,241,363 | B2 | 8/2012  | Sommerich et al. |
| 8,252,054 | B2 | 8/2012  | Greenhalgh et al. |
| 8,398,713 | B2 | 3/2013  | Weiman          |

(Continued)

*Primary Examiner* — Ellen C Hammond
(74) *Attorney, Agent, or Firm* — David L. King

(57) ABSTRACT

An expandable implant device (100) for insertion between two vertebrae (400) is disclosed. The device (100) has an upper body (20), a lower body (40) and an external retainer band (60). The external retainer band (60) holds the upper body (20) and lower body (40) and has an inner surface having a plurality or set of upper ratchet teeth (80U) sloped for allowing upward movement and a plurality or set of lower ratchet teeth (80L) for allowing downward movement. The ratchet teeth (80) of the upper body (20) are mated or fitted to the upper teeth (80) of the retainer band (60) and the ratchet teeth (82) of the lower body (40) are mated or fitted to the lower ratchet teeth (82) of the retainer band (60). The height of the device (100) is increased by upward movement of the upper body (20) and downward movement of the lower body (40).

4 Claims, 7 Drawing Sheets

(56) References Cited

U.S. PATENT DOCUMENTS

| | | |
|---|---|---|
| 8,444,692 B2 | 5/2013 | Michelson |
| 8,535,380 B2 | 9/2013 | Greenhalgh et al. |
| 8,540,770 B2 | 9/2013 | Woodburn et al. |
| 2004/0133280 A1 | 7/2004 | Trieu |
| 2004/0249461 A1 | 12/2004 | Ferree |
| 2007/0255409 A1 | 11/2007 | Dickson et al. |
| 2008/0167720 A1 | 7/2008 | Melkent |
| 2012/0197403 A1* | 8/2012 | Merves .................... A61F 2/44 623/17.16 |
| 2013/0085572 A1 | 4/2013 | Glerum et al. |
| 2013/0211526 A1 | 8/2013 | Alheidt et al. |

* cited by examiner

EXPANDABLE SPINAL IMPLANT

RELATED APPLICATIONS

The present invention is a division of co-pending U.S. application Ser. No. 14/259,639 entitled, "IMPROVED EXPANDABLE SPINAL IMPLANT" filed on Apr. 23, 2014.

TECHNICAL FIELD

The present invention relates to spinal implants generally, more particularly to an improved expandable spinal implant.

BACKGROUND OF THE INVENTION

Spinal stabilization can be achieved by providing an interbody implant. Some of these implants are bone, PEEK, solid titanium or similar non-bone implant material and some are hollow implants that provide for inclusion of a bone graft or other suitable material to facilitate bony union of the vertebrae.

Interbody implants can be inserted into the disc space through an anterior, posterior or lateral approach. In some systems, the implants are inserted into a bore formed between adjacent vertebral bodies in the cortical endplates and can extend into the cancellous bone deep to the cortical endplates. Implant size is typically selected such that the implants force the vertebrae apart to cause tensing of the vertebral annulus and other soft tissue structures surrounding the joint space. Tensing the soft tissues surrounding the joint space results in the vertebrae exerting compressive forces on the implant to maintain the implant in place.

It has been found desirable to keep the surgical opening as small as practical while still having sufficient room to insert the implant device and the end of an elongated tool or insertion instrument.

Advantageously, if the implant size could be reduced further that would allow the surgical opening to be reduced; however, once implanted the device needs to be expandable to provide sufficient spacing of the vertebrae.

A whole class of expandable interbody implant devices have been developed for this purpose. Some prior art devices use hydraulic expansion or inflatable balloons. Some devices are stackable elements piled on themselves to raise their height. Some use rotatable screw jack designs. Some are wedges that have a fixed hinged end and an opposite expandable end. All of the rotatable expandable devices using screw threads require the device to be round cylinders or posts.

One of the problems of such devices is the amount of post insertion manipulation required to reach a fully expanded properly space height is tedious and time consuming. Secondly, additional set screws or locking elements are often required to keep the device at its proper size. Thirdly, the devices of a circular shape are not the best fit for the adjacent vertebrae being spaced. Fourth, most of the devices have the internal space occupied with mechanisms limiting the amount of bone growth material available for packing the implants.

The wedge type implants generally contact the bone on an angle and expandable wedges when expanded simply expand on an angle not parallel to the vertebrae surface. This places localized high loading between the vertebrae because the wedge surfaces are not parallel to the vertebrae.

These and other limitations in the prior art have been corrected and solved by the present invention as disclosed herein.

SUMMARY OF THE INVENTION

An expandable implant device for insertion between two vertebrae is disclosed. The device has an upper body, a lower body and an external retainer band. The upper body has an interior surface forming a hollow cavity and an exterior surface having a plurality of ratchet teeth sloped to allow upward movement. The lower body has an interior surface forming a hollow cavity and an exterior surface having a plurality of ratchet teeth sloped to allow downward movement. The external retainer band holds the upper body and lower body and has an inner surface having a plurality of upper ratchet teeth sloped for allowing upward movement and a plurality of lower ratchet teeth for allowing downward movement. The ratchet teeth of the upper body are mated or fitted to the upper teeth of the retainer band and the ratchet teeth of the lower body are mated or fitted to the lower ratchet teeth of the retainer band. The height of the device is increased by upward movement of the upper body and downward movement of the lower body. The movement is linear and maintained parallel to the ratchet teeth as the bodies move relative to the retainer band. The remaining ratchet teeth mated or fitted to the ratchet teeth of the retainer are locked to resist compressive movement of the extended upper and lower bodies. The retainer band has at least one end with a slotted opening. The upper body and lower body are spaced and separated by the retainer band. The vertical movement of the bodies is parallel and horizontal relative to the vertebrae being spaced. The movement of the upper and lower bodies increases a hollow cavity size or volume formed by the retainer band and spaced apart bodies.

Each of the upper body and lower body has a lip at a respective outermost upper surface of the upper body and outermost lower surface of the lower body. The lip extends along a peripheral edge of the respective body. The innermost surfaces of the upper and lower bodies have a stepped edge extending along a peripheral edge. The stepped edges are abutting or in close proximity when the bodies are fully unexpanded. Preferably, the plurality of ratchet teeth in both the upper and lower body extend from the step to the lip along two opposing portions of each upper and lower body.

The expandable implant has a fully unexpanded height of 10 mm or less. The expandable implant has a fully expanded height of at least 3 mm or preferably at least 5 mm greater than the unexpanded height.

The retainer band has a plurality of holes between the upper and lower sets of ratchet teeth. The holes are angled to receive a tool to disengage or unlock the mated or fitted ratchet teeth to lower the upper or lower bodies into a retracted unexpanded height. The expandable implant device further has a separate insertion tool. The insertion tool has an end sized to fit through said slotted opening of the retainer band and extend toward an opposite end, the tool allows insertion of the implant device between the two vertebrae to be spaced. The insertion tool has an end sized to fit inside the implant device between the upper and lower bodies. Preferably the end is fixed to a shaft on the insertion tool. Rotation of the shaft rotates said end into contact with the upper and lower bodies inside said retainer band and wherein further rotation simultaneously moves both upper and lower bodies to an expanded height. Rotation to a full expansion height occurs at a rotation of 90 degrees or more of the end. The height of the expanded device is controlled by the number of ratchet teeth passed on movement of the bodies. When the expansion height is set, the upper and lower bodies are locked automatically relative to the retainer band at the height by the respective remaining mated or fitted together ratchet teeth.

The invention further includes a method of insertion of an expandable implant device between two vertebrae comprises the steps of: providing an unexpanded implant device, having an upper body, lower body and a retainer band for holding said upper and lower bodies, the retainer having a slotted opening; providing an insertion tool having an end sized to fit said slotted opening and fixed to a shaft or handle; inserting the end of the insertion tool into said slotted opening to attach the device to said insertion tool; inserting the device into a prepared surgical opening and between two vertebrae to be spaced apart; rotating the shaft or handle causing the end to rotate into contact with the upper and lower bodies and continuing said rotation to the desired height and stopping rotation locks said device at the height; and reversing rotation of the end to align with the slotted opening and retracting said tool. The method may include packing the implant device with bone growth material through said slotted opening. Preferably, the method further includes the steps of: inserting a wire to the location between the vertebrae where the implant is to be positioned; and guiding the implant affixed to the insertion tool to the location by passing the wire through the implant, more preferably, wherein the end and the shaft of said insertion tool have a passageway; and inserting said guide wire through the end and shaft as well as the implant device.

BRIEF DESCRIPTION OF THE DRAWINGS

The invention will be described by way of example and with reference to the accompanying drawings in which.

DETAILED DESCRIPTION OF THE INVENTION

Figure 1:
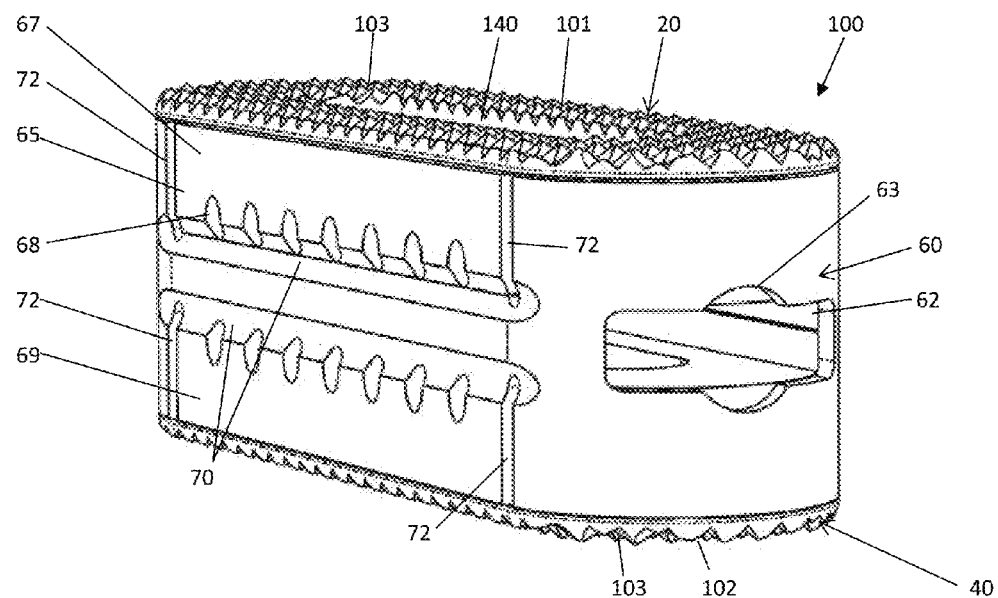
FIG. 1 is a perspective view of the expandable implant device of the present invention.

With reference to FIG. 1, the expandable implant device 100 made according to the present invention is illustrated. As shown, the implant device 100 is in the fully retracted unexpanded condition. As shown, the device 100 has an upper body 20, a lower body 40 and a retainer band 60 encircling both the upper and lower body. In a preferred embodiment, the upper and lower bodies are made of a plastic or synthetic material. In a preferred embodiment, this material is PEEK (PolyEtherEtherKetone) although alternative materials can be used for either of the upper or lower body. The top outer surface 101 of the upper body 20 and the bottom outer surface 102 of the lower body 40 are provided with a plurality of facets or ridges 103 or roughened surfaces. These surfaces 101, 102 will contact the vertebrae when installed and expanded and provide a gripping surface to which the implant is securely held when expanded between the two spaced vertebrae.

As shown, the expandable implant device 100 in the illustrations is a substantially oblong oval shaped device with straight sides with curved ends. The device can vary in size having a length of 20 to 40 mm, preferably 26 to 34 mm and a height of 5 to 15 mm, preferably 8 to 12 mm, in the example about 9 mm. The width of the device is between 8 to 15 mm or 8 to 12 mm, as shown 9 mm. While the two sides are illustrated as straight and parallel in their respective lengths, each of the sides could have an outwardly bowed center increasing the size and surface area. Alternatively, the two sides can take on a curved configuration of a banana shape or parallel crescents along the length to more optimally fit the space between the vertebrae. All these shapes can employ the inventive features of the device 100.

Figure 1A:
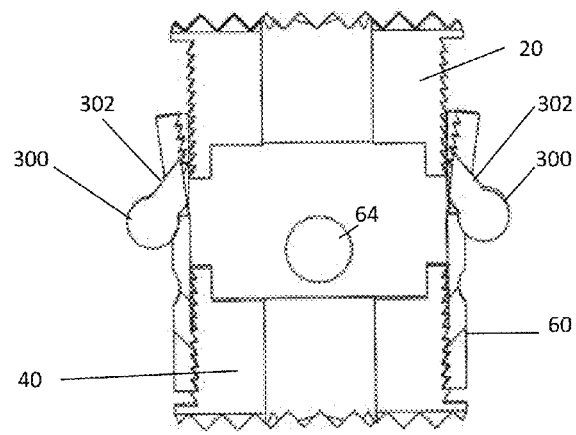
FIG. 1A is a view showing how the retainer band is deflected to allow insertion of the upper and lower body into the unexpanded condition.
Figure 1B:
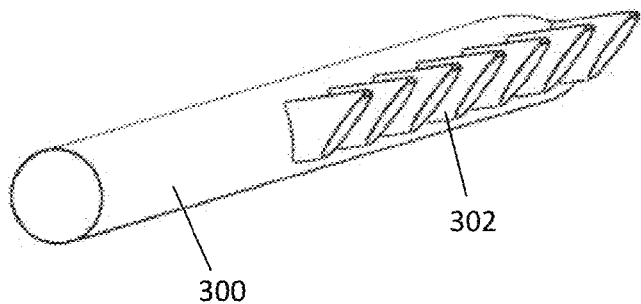
FIG. 1B is an exemplary tool for unlatching the retainer to allow upper and lower bodies to be assembled to the device in a fully retracted unexpanded condition.
Figure 2:
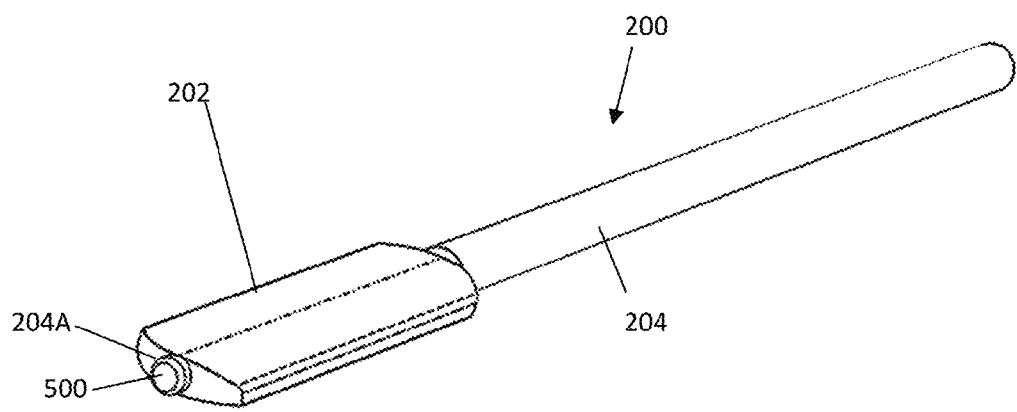
FIG. 2 is a perspective view of the insertion tool of the present invention.
Figure 6:
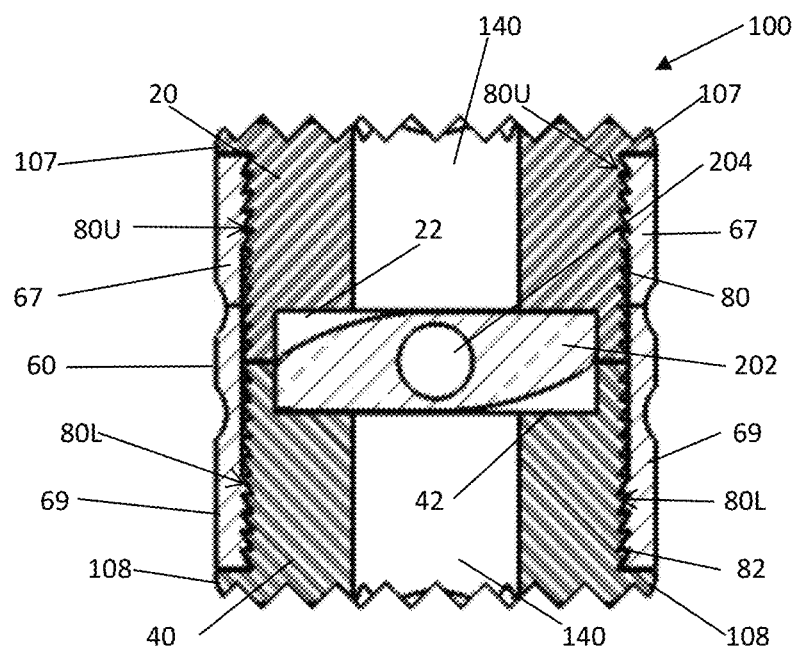
FIG. 6 is a cross sectional view of the device taken along line 6-6 of FIG. 1.

With reference to the retainer band 60, at one end is shown a slot opening 62 with a circular center 63 cut through the band 60. This slot opening 62 is provided for the insertion tool 200, shown in FIG. 2, to enable its end 202 to slip through and into the implant device 100 up to and including portions of the shaft 204 of the insertion tool 200. Along the sides 65, 66 of the retainer band 60 is shown a plurality of holes 68 extending on an angle originating partially into a curved depression 70 in both an upper portion 67 of the retainer band 60 and a lower portion 69 of the retainer band. These holes 68 are spaced between slots 72 as illustrated. The slots 72 and depressions 70 facilitate retracting the portions 67, 69 of the retainer band 60 outwardly. A tool 300, shown partially in FIG. 1B, has ends 302 inserted into one or more of the holes 68 and pried in such a fashion that the portion 67, 69 of the retainer 60 can flex outwardly. When both sides 65, 66 of the retainer band 60 have these portions flexed outwardly, as shown in FIG. 1A, the body portion either upper body 20 or lower body 40 can then be inserted fully into the retainer band 60. This enables the implant device 100 to be pre-assembled in a fully retracted condition. This fully retracted position is also illustrated in the cross sectional view FIG. 6. As shown in FIG. 6, the top upper surface 101 and bottom lower surface 102 of the respective upper and lower bodies have a lip 107, 108 which comes into close proximity or contact with the retainer band 60. Accordingly, when fully seated, the implant 100 is at its lowest possible vertical height ($H_U$). This fully retracted position creates a very low profile implant device that enables the device 100 to be slipped into a smaller surgical opening than otherwise would be possible.

Figure 3:
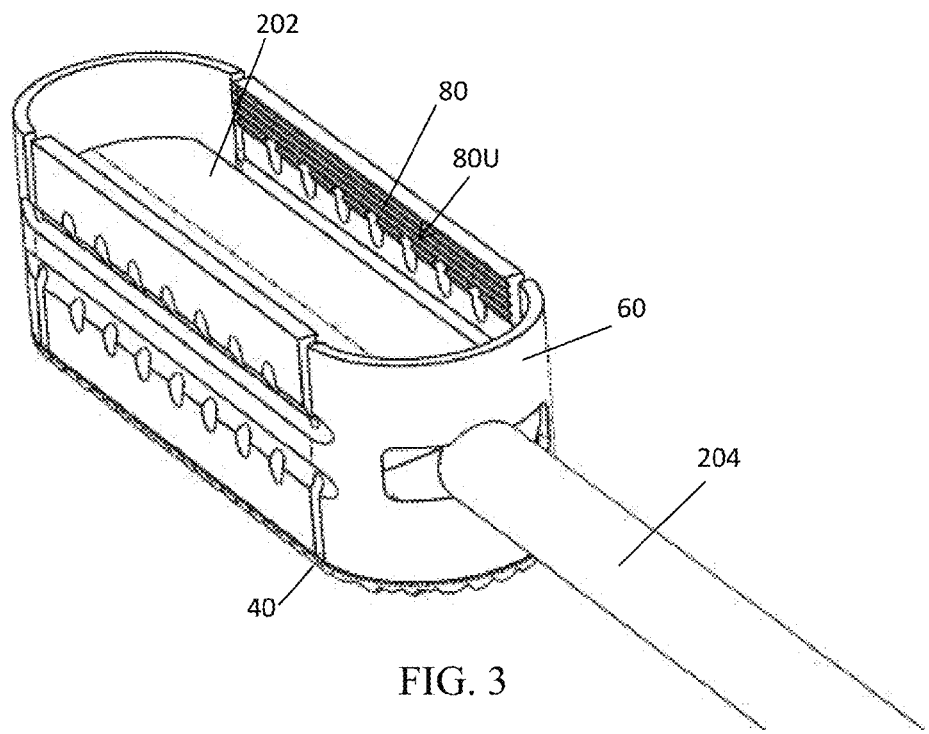
FIG. 3 is a perspective view showing the insertion tool end fitted through a slotted opening in the retainer band where the upper body is removed to enable viewing the end inside the implant with the lower end unextended.
Figure 4:
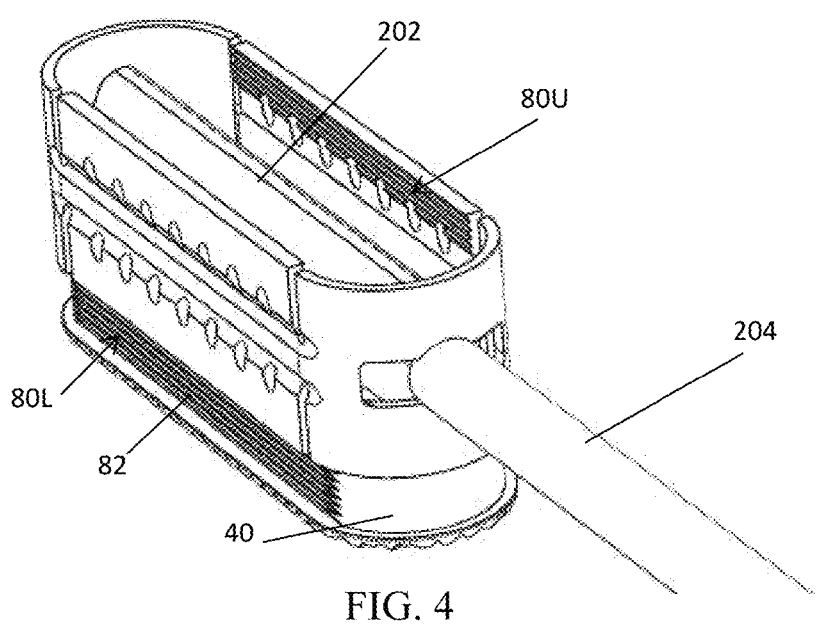
FIG. 4 is a view similar to FIG. 3, but where the end has been rotated showing the lower portion extended.
Figure 5:
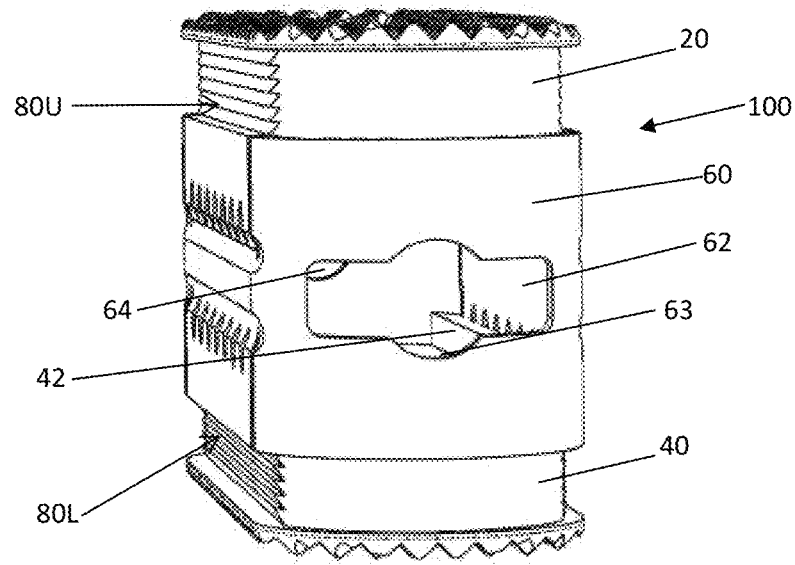
FIG. 5 is a perspective view of the implant device extended without the insertion tool.

As shown in FIG. 3, which has the upper body 20 removed so that the insertion tool 200 and end 202 are clearly visible, it is important to observe that the insertion tool 200 when slipped into the implant device 100, as shown, extends fully into the opposite end of the implant device 100. As shown in FIG. 5, where the insertion tool 200 is removed, a circular opening 64 at the opposite end of the device 100 creates an aperture through which the shaft end 204A of the insertion tool 200 can be inserted. This stabilizes the tool 200 so that upon rotation of the shaft 204, the end 204A can also properly rotate in a uniform fashion so that it is parallel to both the upper body 20 and lower body 40 at the times of rotation. As can be appreciated in FIG. 3, the retainer band 60 along its sides 65, 66 has a plurality of ratchet teeth 80, 82. In FIG. 6 these ratchet teeth 80, 82 are provided on both sides of the retainer band 60 on an upper portion 67 and a lower portion 69 of the retainer band 60, those on the upper portion 67 being a set 80U, those on the lower portion being a set 80L.

Figure 7:
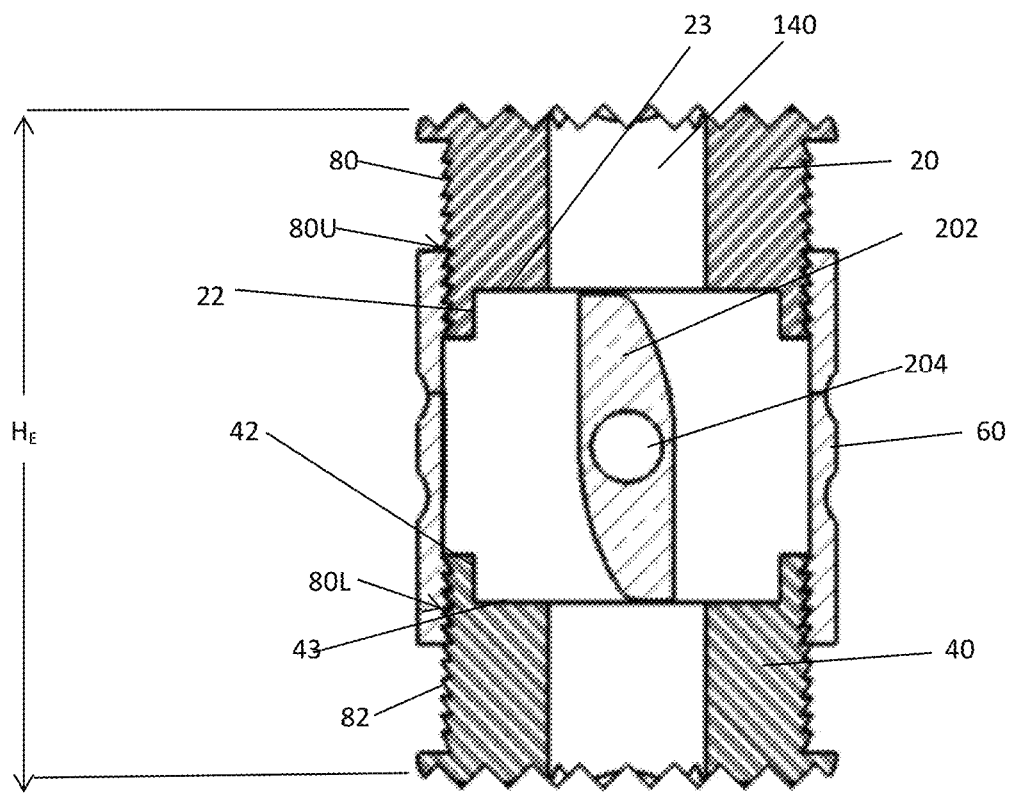
FIG. 7 is a cross sectional view of the device from FIG. 6 wherein the end of the insertion tool is shown rotated expanding the implant device.
Figure 8A:
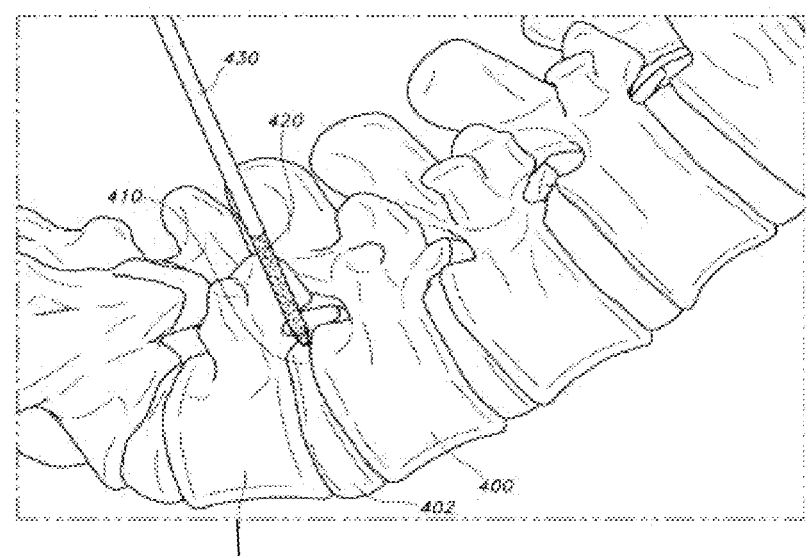
FIGS. 8A-8E are views of an exemplary method of using the device in a vertebrae repair showing that portion of the spine.
Figure 8B:
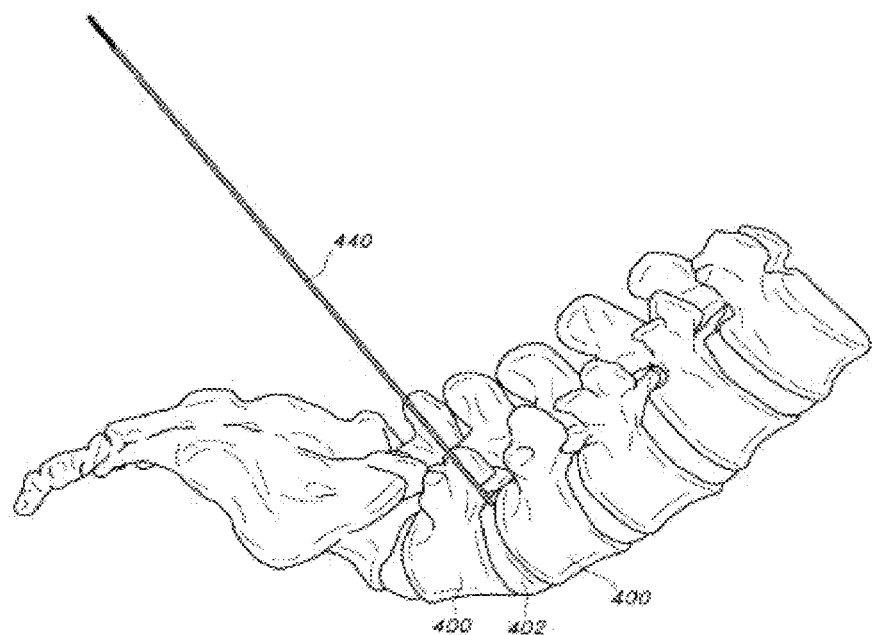
Figure 8C:
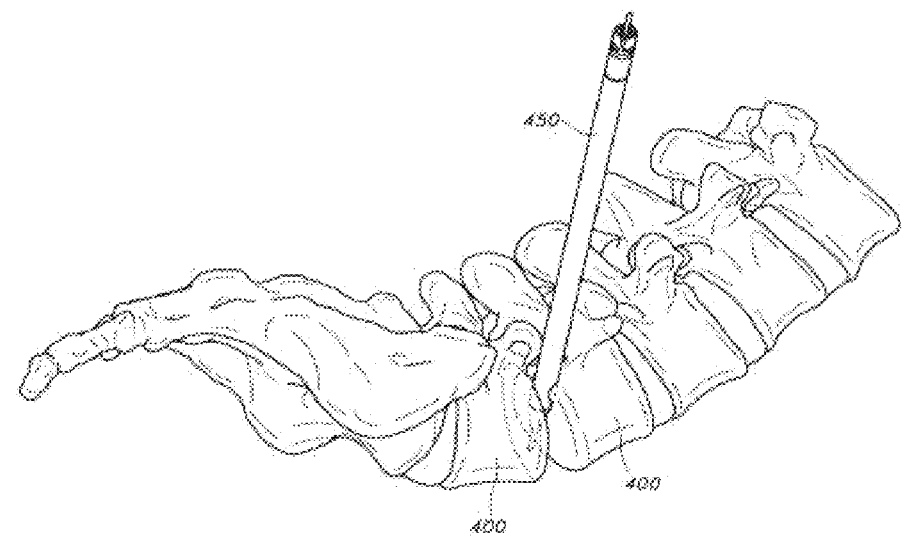
Figure 8D:
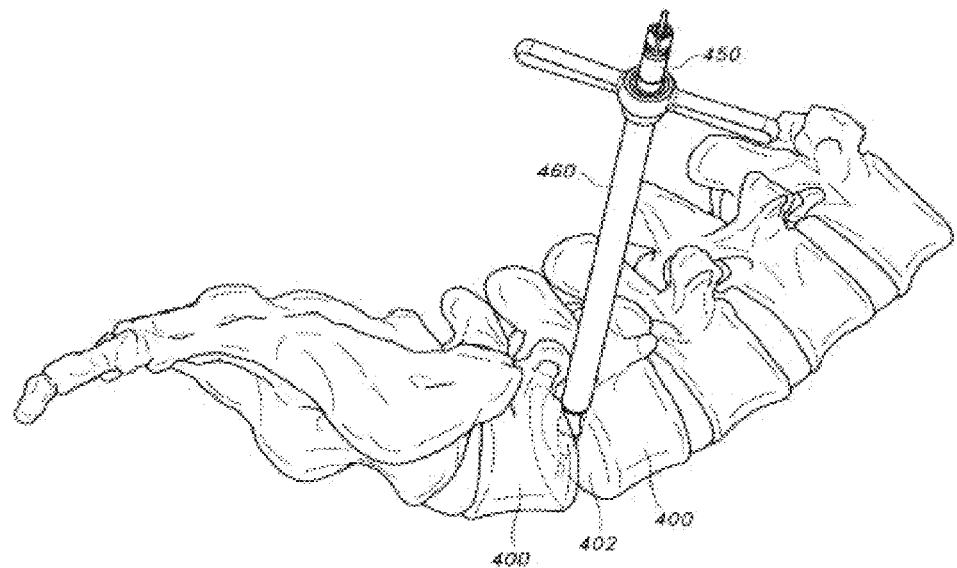
Figure 8E:
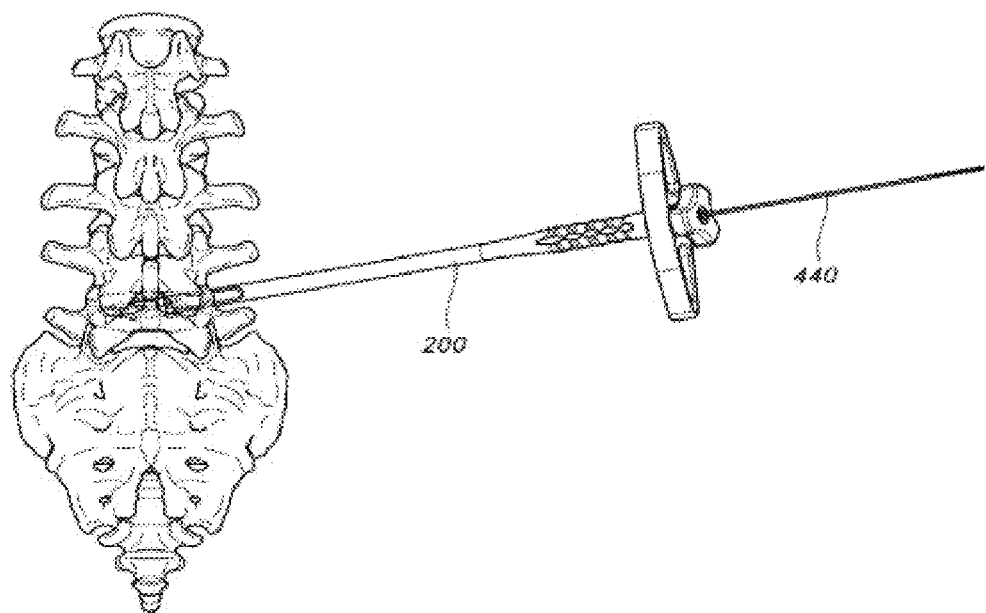

With reference to FIG. 6, it is important to note in the cross sectional view that the retainer band 60 has two sets of ratchet teeth 80, 82, an upper set 80U along each side has the teeth sloped in a direction such that the teeth 80 allow the implant device 100 upper body 20 to freely move in an upward or outward direction and the lower set 80L teeth 82 are sloped in such a fashion that the lower body 40 can be pushed in an outward or downward direction with ease. These sets of ratchet teeth 80, 82 enable the upper body 20 and lower body 40 to move simultaneously upon rotation of the insertion tool 200. This rotation is best shown in FIG. 6 in the retracted position where the end 202 is shown in a generally horizontal position and both upper and lower bodies 20, 40 are shown in the fully retracted position. FIG. 7 shows the end 202 of the insertion tool 200 has been rotated approximately 90 degrees wherein the upper body 20 and lower body 40 have been moved outwardly, the upper body 20 moving in an upward direction and the lower body 40 moving in a downward direction. This increases the effective or expanded height ($H_E$) of the device 100 substantially. The device can be moved in increments as low as one ratchet tooth 80, 82 which corresponds to an increase in size of fractions of mm's to as much as 5 mm or more in a fully expanded height ($H_E$) condition. In the fully expanded condition of FIG. 7, the remaining mated or fitted ratchet teeth 80, 82 between the retainer band 60 and the upper or lower body 20, 40 hold the device 100 into position. It is important to note, the teeth 80, 82 are designed in such a fashion that they freely allow an outward movement relative to the retainer band 60, but resist any inward movement by compressive forces due the shape of the teeth which can move in one outward direction only based on the configuration of the teeth surface. The teeth surface being either inclined slightly inwardly or at a minimum flat, in such a fashion that the teeth 80, 82 cannot move inwardly unless the retainer band 60 is flexed outwardly as previously described using an external tool 300 into the sloped hole openings 68 to bend the retainer band sides 65, 66 outwardly so the body 20 or 40 can be retracted. During normal use, it is unnecessary to move the implant device 100 vertically down as the surgeon when installing the device 100 already in the retracted position will simply bring the implant 100 to its proper location between the two spaced vertebrae and will rotate the shaft 204 while doing so expand the device 100 to the position at which he wants the vertebrae to be spaced. Once this occurs, the handle or shaft 204 can be reverse rotated or relaxed in such a fashion that the end 202 is no longer pushing against the interior surface of either the upper body 20 or lower body 40.

As shown in FIGS. 6 and 7, it is important to note that around the peripheral inward innermost surfaces of the upper 20 or lower 40 body is a step configuration. This step configuration 22, 42 provides a working surface 23, 43 around the entire peripheral interior of the upper body and lower body. This enables the insertion tool end to push against the surfaces 23, 43 as it is lifting or pushing downwardly the respective body 20 or 40. Because of the stepped configuration, the surfaces 23, 43 provided ensure the end 202 of the insertion tool 200 is always in contact with the upper and lower body during this rotation, if not along the sides as it is initially lifting up, at least at both ends of the bodies 20 or 40 as the insertion tool 200 end 202 is rotated in an almost vertical condition as shown in FIG. 7. It is important note in FIG. 6, that the space between the upper body 20 and lower body 40 between the interior surfaces form a hollow cavity 140 into which not only the end 202 of the insertion tool 200 can be inserted, but bone growth material can be inserted either on a preassembly into the device or preferably after the expandable implant device 100 has been inserted into the spine. As shown in FIGS. 1 and 6, the implant device 100 upper body 20 and lower body 40 has an oval opening at the top and bottom. This oval opening provides easy packing of the bone growth material on preassembly, however, once assembled these areas are blocked by the vertebrae. Accordingly, when the insertion tool is removed, the cavity 140, as shown in FIG. 7 in the expanded condition, is enlarged greatly resulting in the volumetric space being increased dramatically, by the expansion of the implant device 100. When this occurs, additional bone growth material or all the bone growth material can be inserted when the insertion tool 200 is removed. Once the insertion tool 200 is removed, the bone growth material (not shown) can fully pack the implant device 100 through the slotted opening 62 and is in direct contact with the surface of the vertebrae through the oval openings of the cavity 140 at the top surface 101 and bottom surface 102. It is important to appreciate that the ratchet teeth 80, 82 on each body that extend from the peripheral step 22, 42 to the lip 107, 108 on each upper or lower body 20, 40 and are designed so that the slope permits the proper movement. The complimentary or mating teeth of the retainer band 60 are similarly sloped. This enables the device 100 to fully expand with minimal resistance; however, they block any retraction and lock the device 100 against any compressive load tending to move the device upper body 20 or lower body 40 inwardly. This automatic locking feature is a great advantage in that no additional tools, set screws or other mechanical instruments are required. Once the device 100 is inserted and the insertion tool 200 is rotated moving the implant 100 into its expanded position and the insertion tool 200 is then reverse rotated back to its horizontal position so that it can be withdrawn through the slotted opening 62, the manipulation is complete. The outward movement is facilitated by the sloped teeth surface acting as a ramp, typically less than 30 degrees off vertical, preferably 20 degrees or less. The inward movement is blocked by the opposite tooth surface being oriented horizontal at 90 degrees or less than 90 degrees off vertical so compressive forces pushing the bodies inwardly are stopped or even sloped directionally to increase the bite and oppose any lateral detaching forces.

With reference to the insertion tool 200, it is noted that the insertion tool 200 can have a hollow hole 500 extending all the way through the shaft 204 from one end to the other. This hollow hole 500 provides a means or access for which a K wire can be slipped through the insertion tool 200 and the implant device 100. During the surgical procedure, it is preferable that the insertion tool 200 is fully inserted into the implant device 100 and that a pre-inserted K wire that has been placed in the location where the implant device 100 is to be directed to its preferred position in between the vertebrae in such a fashion that as the surgeon inserts the implant device 100 with the insertion tool 200 securely holding the device 100, he may then be guided to the proper location by use of the K wire. To further this procedure, applicants have provided FIGS. 8A-8E showing some of the actual insertion steps of an implant device insertion.

As illustrated in FIG. 1, the expandable implant device 100 has two opposing longitudinal extending outer surfaces with gripping facets 103 each defining ridged surfaces 101, 102. The ridged gripping surfaces 101, 102 are meant to assist with the implant's ability to grip the adjacent bone structure. In one aspect, the ridges are angled in order to assist in preventing the implant from backing out.

Sometimes, it is beneficial to have the means with which to promote bone growth and/or fusion. In one aspect, the implant device 100 further defines an implant cavity 140 in communication with the implant aperture and substantially open to at least one, or both, of the gripping surfaces 101, 102. In this aspect, bone graft material or bone cement can be introduced into the implant cavity 140. The bone graft material can be, for example, autologous bone, allograft bone, bone substitute, osteoinductive agents, and the like.

The implant 100 itself comprises a biocompatible material, capable of being inserted into the body. In one aspect, the bio-compatible material for the upper and lower body is selected from the group consisting of PolyEtherEtherKetone, ceramic, allograft bone, and PolyEtherEtherKetone with $BaSO_4$. Other biocompatible materials are also contemplated. The retainer band is preferably made of titanium. To facilitate a better understanding of how the present inventive expandable implant can be used, exemplary methods of the procedure are provided. These methods are as described in U.S. Pat. No. 8,496,709 entitled "Spinal Implant" granted on Jul. 30, 2013 and commonly owned by assignee Amendia, Inc. of Atlanta, Ga.; the contents of which are incorporated herein by reference in its entirety.

Also presented herein is an exemplary percutaneous fusion method to correct disc compression. The method, in one aspect illustrated in FIGS. 8A-8E, comprises making a posterolateral incision to access the desired spinal motion segment; determining a target level of the disc space 402 between adjacent vertebral bodies 400 for implantation of an implant; locating a path to the disc space at the target level; inserting a guide wire 440 to maintain a path to the disc space 402; sliding the spinal implant along the guide wire 440 to position it into the disc space at the desired position; removing the guide wire; and fixating at least a portion of the desired spinal motion segment.

This first step comprises making a posterolateral incision to access the desired spinal motion segment. In one aspect, the initial access point can be made through Kambin's Triangle 410. Kambin's Triangle, as those skilled in the art will appreciate, is the site of surgical access for posterolateral endoscopic discectomy. It is defined as a right triangle over the dorsolateral disc. The hypotenuse is the exiting nerve, the base (width) is the superior border of the caudal vertebra, and the height is the traversing nerve root.

The method also comprises determining the target level of the disc space between adjacent vertebral bodies 400. Once the target level is established, the method comprises locating a path to the disc space at the target level. This can be accomplished, for example, using a nerve monitoring probe 420 with a transfer sleeve 430. The nerve monitoring probe can measure the proximity of the exiting nerve root. Once measured, in an exemplified aspect, the probe 420 can then be removed, leaving the transfer sleeve 430 in place. In one aspect, the nerve monitoring probe comprises an EMG Navigation system, comprising a blunt-tipped monopolar probe and an exchange cannula.

The method also comprises inserting a guide wire through the transfer sleeve to maintain a path to the disc space. In one aspect, the guide wire 440 can be a Kirschner wire or k-wire. After insertion of the guide wire, one aspect of the method comprises removing the transfer sleeve and placing a dilator 450 over the guide wire. The dilator 450 can be driven into the disc space 402 to distract the vertebral bodies 400.

In one aspect, the next step comprises positioning an access portal 460 into the disc space. For instance, in one exemplified aspect, the surgeon can slide the access portal 460 over the dilator and use an impact sleeve with a mallet to lodge the portal into the disc space. The dilator and guide wire can then be removed, leaving the access portal in place.

In a further aspect, the method can comprise performing a discectomy and decorticating the vertebral endplates. In an exemplified aspect, a drill can be used to access the nucleus and prepare the area for other discectomy instruments. For example, and not meant to be limiting, a disc shaper, can be used for endplate preparation. The surgeon may elect to remove some of the loose disc material at this point. As such, a pituitary rongeur can be used. In another aspect, a disc cutter can be used to accomplish a thorough discectomy. After which, the pituitary rongeur can be used again to remove remaining disc remnants In one aspect, a bone graft (not shown) can then to be introduced. As one skilled in the art can appreciate, this can be accomplished through the portal using a tube and plunger system. In one aspect, the bone graft is a sentinel bone graft. The surgeon can then re-introduce the guide wire 440 and remove the access portal 460.

With input from pre-surgical radiographic film, the next step can comprise determining the height of an adjacent level healthy disc to assist with the selection of the proper amount implant. The size of the implant 100 can be easily determined avoiding the need to be confirmed with a paddle trial or a solid body trial. In the U.S. Pat. No. 8,496,709; to do so, the surgeon had to first insert the trial implant along a path, guided by the guide wire. An insertion tool 200, as described herein above, had been used. Once inserted, if the selected trial implant cannot be rotated into an erect position, the surgeon could then step down to a smaller size. Alternately, if the selected trail can be rotated into an erect position without much frictional resistance, the surgeon could choose the next larger size. Several iterations were necessary to achieve the correctly sized implant. In the present invention using the expandable implant, this procedure is unnecessary, saving much time.

As described herein above, in one aspect, the implant 100 comprises an implant cavity 140. As such, the method comprises, after determining the appropriate implant height, loading graft material into the implant cavity and connecting the implant to the insertion tool and following the guide wire to insert the implant. Imaging technology can be used to verify the correct location of the implant. In one aspect, fluorographic imaging can be used to watch radiographic markers in order to determine the correct location of the implant. In one aspect, as determined by the surgeon, when the images show the radiographic markers evenly placed on each side of the spinous processes, the implant is placed properly. Once the implant is placed properly, the surgeon can then rotate the insertion tool up to 90 degrees or more expanding the implant device to the desired height and release it from the insertion tool 200.

As illustrated, the sets of ratchet teeth 80U, 80L extend lengthwise in parallel rows of teeth 80, 82 so as the upper body 20 and lower body 40 move relative to the retainer 60, the movement ratchets outwardly tooth by tooth in a controlled and maintained parallel relationship to the length of the teeth avoiding or preventing any angular tilting or cocking. This insures the expansion of the bone contacting outer surfaces 101, 102 is accomplished uniformly, evenly and simultaneously. While the direction or path of the movement is clearly perpendicular to the length of the teeth.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A method of insertion of an expandable implant device between two vertebrae comprises the steps of:
    providing an unexpanded implant device, having an upper body, lower body and a retainer band for holding said upper and lower bodies, the retainer having a slotted opening;
    providing an insertion tool having an end sized to fit said slotted opening and fixed to a shaft or handle;
    inserting the end of the insertion tool into said slotted opening to attach the device to said insertion tool;
    inserting the device into a prepared surgical opening or between two vertebrae to be spaced apart;
    rotating the shaft or handle causing the end to rotate into contact with the upper and lower bodies and continuing said rotation to the desired height and stopping rotation locks said device at the height; and
    reversing rotation of the end to align with the slotted opening and retracting said tool.

2. The method of insertion of an expandable implant device between two vertebrae of claim 1 further comprises packing the implant device with bone growth material through said slotted opening.

3. The method of insertion of an expandable implant device between two vertebrae of claim 1 further comprises the steps of:
    inserting a wire to the location between the vertebrae where the implant is to be positioned; and
    guiding the implant affixed to the insertion tool to the location by passing the wire through the implant.

4. The method of insertion of an expandable implant device between two vertebrae of claim 3 wherein the end and the shaft of said insertion tool have a passageway; and inserting said guide wire through the end and shaft as well as the implant device.

* * * * *